United States Patent [19]
Oomura

[11] Patent Number: 5,891,848
[45] Date of Patent: Apr. 6, 1999

[54] PEPTIDE FRAGMENTS

[75] Inventor: Yutaka Oomura, Katoh-gun, Japan

[73] Assignees: Nippon Zoki Pharmaceutical Co., Ltd., Osaka; Ajinomoto Co., Inc., Tokyo, both of Japan

[21] Appl. No.: 637,418

[22] Filed: Apr. 25, 1996

[30] Foreign Application Priority Data

Apr. 25, 1995 [JP] Japan ................................. 7-125947

[51] Int. Cl.⁶ .................................................. A61K 38/00
[52] U.S. Cl. .............................. 514/12; 514/14; 530/324; 530/399
[58] Field of Search .................. 514/12, 14; 530/324, 530/399

[56] References Cited

U.S. PATENT DOCUMENTS 5,401,832  3/1995  Linemeyer et al. .................... 530/399

FOREIGN PATENT DOCUMENTS

| 0388226 | 9/1990 | European Pat. Off. |
| 3275631 | 12/1906 | Japan . |
| 9308828 | 5/1993 | WIPO . |
| 9412201 | 6/1994 | WIPO . |

OTHER PUBLICATIONS

Li, et al., "Fibroblast Growth Factor Receptor–1 in the Lateral Hypothalamic Area Regulates Food Intake," *Experimental Neurology* 137, 318–323 (Feb. 1996).

Chemical Abstract No. 170732x, vol. 121, No. 15, Oct. 10, 1994, p. 143.

Chemical Abstract No. 251144y, vol. 124, No. 19, May 6, 1996, p. 222.

Yamamoto, et al., "Effects of indeloxazine hydrochloride on passive avoidance behavior of senescence–accelerated mice," *European Journal of Pharmacology*, 166 (1989) 345–348.

Flood, et al., "Effect on memory Processing by D–cycloserine, an agonist of the NMDA/glycine receptor," *European Journal of Pharmacology*, 221 (1992) 249–254.

Miyamoto, et al., "Effects of a sustained release formulation of thyrotropin–releasing hormone on behavioral abnormalties in senescence–accelerated mice," *European Journal Pharmacology*, 271 (1994) 357–366.

Nishizawa, et al., "Effects of Kamikihi–To, a Traditional Chinese Medicine on Passive and Conditioned Avoidance Performance Impairment in Senescence Accelerated Mouse (SAM)," *Japan. J. Pharmacol.*, 54, 375–382 (1990).

Matsui, et al., "S–Adenosyl–L–methionine prevents ischemic neuronal death," *European Journal of Pharmacology*, 144 (1987) 211–216.

Bottliglieri et al., "The Clinical Potential of Ademetionine (S–Adenosylmethionine) in Neurological Disorders," *Drugs*, 48(2) 137–152 (1994).

Sasaki et al., *Obesity Research*, vol. 3, Suppl. 5, 697–706, Dec. 1995.

Oomura et al., Mol. Med., 30(8), pp. 1018–1028, 1993.

Hcaplus AN:1996:228149, Sasaki et al., *Obes. Res.*, 3 (Suppl. 5), 697S–706S, 1995.

Sasaki et al., "Effects of Fibroblast Growth Factors and Related Peptides on Food Intake by Rats", *Physiol. Behav.* (1994), 56(2), 211–218.

*Primary Examiner*—Cecilia J. Tsang
*Assistant Examiner*—C. Delacroix-Muirheid
*Attorney, Agent, or Firm*—Fisher, Christen & Sabol

[57] ABSTRACT

Peptide fragments and their pharmaceutically acceptable salts, and therapeutic agents containing one or more of them as an effective component possess excellent therapeutic activity for improving cerebral function and protecting cerebral neurons and are useful as pharmaceutical agents. The peptide fragments of the present invention are amino acid residue peptide fragments of acid fibroblast growth factor (aFGF) of mammalian animals or humans which do not contain cysteine at the 16-position. The compounds include a 1–29 amino acid residue peptide fragment of acid fibroblast growth factor in which cysteine, an amino acid at the 16-position, is substituted with another amino acid, such as alanine, serine, or glutamic acid, and pharmaceutically acceptable salts thereof. The compounds also include a 1–15 amino acid residue fragment of acid fibroblast growth factor of mammalian animals or humans and pharmaceutically acceptable salts thereof. The protein fragments may have an N-terminal group which is in amide form or free form. In a passive avoidance learning test and in a maze-learning test in water, the peptides of the present invention exhibit an excellent action of improving the learning and the remembering ability of senility-accelerated mice in which remembering and learning abilities were reduced. The peptide fragments also exhibit a protective effect against the death of cerebral neurons caused by ischemia. As such, the compounds of the present invention show excellent improvement of brain functions and protection of cerebral neurons. The compounds are useful as a pharmaceutical agent for dementia and other diseases caused by reduction of various brain functions.

13 Claims, 3 Drawing Sheets

PEPTIDE FRAGMENTS

FIELD OF THE INVENTION

The present invention relates to amino acid residue peptide fragments of acid fibroblast growth factor of mammals and to pharmaceutically acceptable salts of the peptide fragments which improve cerebral function and protect cerebral neurons. It also relates to pharmaceutical compositions containing the peptide fragment or its pharmaceutically acceptable salt as an effective ingredient.

BACKGROUND OF THE INVENTION

Fibroblast growth factor (FGF) is a peptidic cell growth factor which exhibits a growing action toward cells such as fibroblast and endothelial cells of blood vessels. Fibroblast growth factor is a general term for a family of several peptides mainly comprising basic FGF and acidic FGF. Acidic FGF (aFGF) is a protein with a molecular weight of about 16 kD comprising 140 amino acid residues. Acidic FGF is widely distributed in various tissues in living organisms. It is especially abundant in the brain and retina. Acidic FGF has been known to exhibit various physiological actions necessary for maintaining the homeostasis of a living body such as new growth of blood vessels due to cell growth action, curing of wounds, curing of ulcers and growth of undifferentiated osteogenic cells, as well as improvement of memory and control of appetite.

As mentioned above, aFGF is a protein having many useful physiological activities. However, organic synthesis of a peptide having as many as 140 amino acid residues requires many steps and operations. The organic synthesis is not economically feasible and, therefore, its use is not practical. Accordingly, gene recombination has been actually utilized but, to obtain a product of uniform quality, high technique is required. Also, unlike in the case of organic synthesis, special facilities are necessary. In addition, FGF has a low organ specificity and has a tendency to conduct neovascular action to give cancer cells. Therefore, its actual application as a pharmaceutical agent is still problematic whereby manufacture of its derivatives and a specific method for administration have been investigated. Further, it is a protein having a molecular weight of 16 kD and, when compared with other peptides having small sizes, there are problems such as antigenicity and incorporating an effective amount into the brain. Consequently, there are still several problems that have to be solved for its actual production as a pharmaceutical, or for meeting certain standards for use in an actual therapy.

There are some cases where, in achieving the activity of physiologically active high-molecular weight substances, the use of the total structure of the maturation protein is not always necessary. Thus, it has been known that even a partial fragment often exhibits the same physiological activity as the parent protein provided that said fragment contains the active moiety of the maturation protein. In addition, when a part of the amino acids participating in the active moiety of the peptide is substituted with other amino acids, it is possible to achieve reinforcement of biological activity, an increase in stability, elongation of duration or effectiveness, improvement in tissue specificity, improvement in incorporation into tissues, reduction of side effects, etc. of the peptide and its partial fragments. The present inventors have conducted investigations on partial peptides of aFGF which have various advantages such as the same physiological activity exhibited by aFGF but which are made by a simple and easy synthesis whereupon they have found the peptides of the present invention.

The peptide fragments of the present invention and their pharmaceutically acceptable salts have a relatively low molecular weight for incorporation into tissues and may be readily synthesized. They exhibit excellent physiological activity for improving cerebral functions and for protection of cerebral neurons.

SUMMARY OF THE INVENTION

The peptide fragments and their pharmaceutically acceptable salts of the present invention exhibit unexpectedly superior action for improving cerebral function and protecting cerebral neurons and are useful for the treatment of diseases and disturbances which adversely affect brain function. The peptide fragments and their salts substantially improve reduced learning ability and memory resulting from senility.

The peptide fragments of the present invention are amino acid residue peptide fragments of acid fibroblast growth factor (aFGF) of mammalian animals or humans which do not contain cysteine at the 16-position. The compounds of the present invention include a 1–29 amino acid residue peptide fragment of acid fibroblast growth factor in which cysteine, an amino acid at the 16-position, is substituted with another amino acid, such as alanine, serine, or glutamic acid, and pharmaceutically acceptable salts thereof. The compounds of the present invention also include a 1–15 amino acid residue fragment of acid fibroblast growth factor of mammalian animals or humans and pharmaceutically acceptable salts thereof. The protein fragments of the present invention may have an N-terminal group which is in amide form or free form.

The present invention also provides pharmaceutical compositions containing at least one of the peptide fragments or at least one salt thereof in a pharmaceutically acceptable amount.

The compounds and pharmaceutical compositions of the present invention may be used in pharmaceutically effective amounts to treat and prevent diseases and conditions resulting in reduced cerebral functions such as diseases caused by degeneration of the brain, cerebrovascular disturbances, infectious and inflammatory diseases of the brain, toxic brain disturbances, head injuries, epilepsy, brain tumors, intracranial hematoma and dialysis brain disease, and ischemic cerebral diseases. They are also useful for improvement of various symptoms accompanied therewith such as hypomnesia, aphasia, disturbance of consciousness, depression, indifference, delusion and confusion.

DETAILED DESCRIPTION OF THE INVENTION

The present invention provides amino acid residue peptide fragments of acid fibroblast growth factor (aFGF) of mammalian animals or humans which do not contain cysteine at the 16-position, and pharmaceutically acceptable salts thereof, which improve cerebral function and protect cerebral neurons and are useful as pharmaceuticals. The peptide fragments may contain another amino acid at the 16-position or they may terminate with the 15-position amino acid.

The peptide fragments in accordance with the present invention include a 1–29 amino acid residue peptide fragment of acid fibroblast growth factor of mammals in which cysteine, an amino acid at the 16-position, is substituted with another amino acid. The aFGF of any mammal may be used provided the amino acid sequence of the aFGF is substantially homologous to that of human aFGF and the same physiological activity as that of human aFGF is available. An example of a non-human aFGF which may be a used is bovine aFGF. Examples of the amino acid which is substituted for cysteine, an amino acid at the 16-position of aFGF, are α-amino acids such as alanine, serine and glutamic acid. With regard to the N-terminal group, although aFGF in a living body is in a free form, an amide form can be easily prepared using a suitable synthetic method. Therefore, the present invention includes such an amide type as well. For example, the peptide fragment of the present invention derived from human aFGF can be represented by the amino acid sequence of the following formula (I). The amino acid residues are described in this specification by a three-letter code regulated by the International Union of Biochemistry (IUB):

In the formula, X is Ala (SEQ ID NO: 2 or SEQ ID NO: 6) Ser (SEQ ID NO: 3 or SEQ ID NO: 7) or Glu (SEQ ID NO: 4 or SEQ ID NO: 8) and Y is OH or NH$_2$.

The formula (II) shows an amino acid sequence of the peptide fragment of the present invention based upon bovine aFGF:

In the formula, X and Y have the same meanings as those in the formula (I) (where X is Ala, see SEQ ID NO: 12 and SEQ ID NO: 16; where X is Ser, see SEQ ID NO: 13 and SEQ ID NO: 17; and where X is Glu, see SEQ ID NO: 14 and SEQ ID NO: 18)

The peptide fragments of the present invention also include a 1–15 amino acid residue fragment of acid fibroblast growth factor of mammals and pharmaceutically acceptable salts thereof. For example, the peptide fragment of the present invention derived from human aFGF can be represented by the amino acid sequence of the following formula (III):

wherein Y is OH or NH$_2$.

The following formula (IV) shows an amino acid sequence of the peptide fragment based upon bovine aFGF:

wherein Y is OH or NH$_2$.

The compounds of the present invention include the pharmaceutically acceptable salts of the peptide fragments. Exemplary salts of the present invention are acid addition salts of the peptide fragments with hydrochloric acid, sulfuric acid, nitric acid, hydrobromic acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluene sulfonic acid, naphthalene sulfonic acid, or sulfanilic acid. Other salts of the present invention include salts of the peptide fragments with: (a) an alkali metal such as sodium and potassium, (b) an alkaline-earth metal such as calcium and magnesium, or (c) other metals such as aluminum.

The pharmaceutically acceptable salts may be manufactured by conventional methods starting from the peptide fragment of the present invention in a free state or free form, or by conversion from one salt to another salt. Amino acid residues of the peptide fragment of the present invention include any and all of their D-form, L-form and DL-form.

The peptide fragment of the present invention may be manufactured by conventional methods used in peptide chemistry syntheses such as solid phase peptide synthesis, liquid phase peptide synthesis and gene technology. Each of the amino acids which constitute the peptide fragment of the present invention may be condensed one after another by the above-mentioned methods. It is also possible to synthesize partial peptides and to then condense the partial peptides to manufacture the final peptide fragment of the present invention.

One example of a solid phase synthesis which is frequently used in the manufacture of peptides comprising scores of amino acid residues which may be used to produce the peptide fragments of the present invention is a fundamental synthetic method reported by Merrifield, et al. in J. Am. Chem. Soc., 85, page 2149 (1964). In this solid phase peptide synthesis an amino acid residue at the C-terminal of the desired peptide is coupled with a suitable resin and then other amino acids are successively condensed therewith so that the peptide chain is elongated to the N-terminal. Thus, the amino acid residue corresponding to the C-terminal where the amino group is protected is bonded with a PAM [4-(hydroxymethyl)phenylacetamidomethyl) resin via a benzyl ester bond or with a BHA (benzhydrylamine) resin or an MBHA (methylbenzhydrylamine) resin via an amide bond whereby the initial stage of the synthetic reaction may be conducted. In case of separation and purification from each of the resins, the C-terminal may be obtained in a free type or free form (where Y in the above formula is OH) and in an amide type or amide form (where Y in the above formula is $NH_2$) and the resin can be chosen depending upon the object. The resin to which one kind of amino acid residue is bonded as such is available in the market and it is convenient to use such a resin. Since the solid phase peptide synthesis utilizes the resin as a carrier, it is convenient when condensation and deblocking are successively carried out by changing the solvents and the process of washing the resin is quite simple as well.

Synthetic methods for peptides as well as condensing agents, protective groups, deblocking methods, solvents, reaction conditions, etc. are mentioned in detail in "Fundamentals and Experiments of Peptide Synthesis" by Nobuo Izumiya, et al. (published by Maruzen Co., Ltd.) and they may be suitably selected in conventional manner depending upon the type of the constituting amino acids of the aimed peptide, availability of the reagents, type of the synthetic devices, etc. In some reactions, protective groups for side chains are not necessary. Also, during the course of synthesis of the peptide fragment or in the final stage, they may be selectively or completely detached by conventional means such as a catalytic reduction or an acid decomposition using anhydrous hydrogen fluoride or trifluoroacetic acid. For example, Arg has an amino acid even in the side chain. Therefore, the amino group participating in the condensation and the amino group located in the guanidino group in the side chain are protected by a tert-butoxycarbonyl group (Boc) or by a p-toluenesulfonyl group (Tos), respectively. So, the amino groups on the side chains are continuously protected until the final stage of the peptide synthesis (in which dicyclohexylcarbodiimide and trifluoroacetic acid are used as a condensing agent and an agent for detaching Boc, respectively) whereupon side reactions caused by the amino group of the guanidino group in the side chain can be prevented.

A brief explanation will be made by taking the case where the above-mentioned Boc is chosen as a protective group for the amino group participating in the condensation as an example. Thus, after the amino acid at the C-terminal of the aimed peptide is condensed with a resin, the group protected with Boc in said amino acid is detached by trifluoroacetic acid. Then, an amino acid (in which the amino group is protected by Boc) to be condensed is added followed by subjecting it to a condensation whereupon a product in which dipeptide is bonded with the resin is prepared. When the same reaction is successively conducted, the peptide chain can be elongated accordingly. Finally, the desired peptide can be liberated from the resin by treatment with anhydrous hydrogen fluoride. In each step of the synthesis, the result of the condensation reaction can be confirmed by means of a ninhydrin reaction or the like. Thus, if the condensation takes place efficiently, free amino group is not present and, therefore, is undetectable by a Kaiser test. Several types of peptide synthesizers where such a principle of peptide synthesis is applied are commercially available and it is possible to conduct an automatic peptide synthesis using such devices.

Usually, a high performance liquid chromatography (HPLC) and an amino acid analysis are combined for confirming whether the synthesized peptide has the desired amino acid sequence.

The present invention is illustrated by the following non-limiting examples:

EXAMPLE 1

This example illustrates the synthesis of a peptide fragment of the present invention using a peptide synthesizer.

A 1–29 amino acid residue peptide fragment of bovine aFGF in which Cys, an amino acid at the 16-position, was substituted with Ala was synthesized using a peptide synthesizer (Model 431A manufactured by Applied Biosystems Japan KK). PAM resin into which Boc-Gly was introduced was used as the resin and each of the amino acids protected by Boc was successively introduced whereupon the desired peptide was synthesized. After removal of the protective groups and the resin, purification was conducted by means of gel filtration and an HPLC. The resulting peptide was confirmed to be substantially pure as a result of the amino acid analysis and the HPLC.

Similarly prepared were: (a) a 1–29 amino acid residue peptide fragment of bovine aFGF in which Cys, an amino acid at the 16-position, was substituted with Ser or Glu, (b) a 1–29 amino acid residue peptide fragment of human aFGF in which Cys, an amino acid at the 16-position, was substituted with Ala, Ser or Glu, and (c) a 1–15 amino acid residue peptide fragment of bovine or human aFGF by using the above-mentioned peptide synthesizer.

EXAMPLE 2

Senility-accelerated mice (SAM-P/8 strain) show physical senility symptoms since their early stage after birth and, at the same time, their abilities for learning and remembering already decrease in the third month from birth. Therefore, they are used as experimental models for dementia. The results of the investigation on the improving action of the peptide of the present invention on cerebral function using said senility-accelerated mice are:

(1) Passive avoidance learning test.

In a passive avoidance learning test, remembering ability of senility-accelerated mice of the SAM-P/8 strain decreases from the third month from birth. The effect of the peptide of the present invention for improving said learning disability was investigated. Thus, a mouse was placed in front of a dark box and its ability to remember what it learned was measured using the time it took to come into the box as an index. Electric current was turned on in the dark box after the mouse came into the box so that an electric shock was applied. When the time until it came into the dark box was longer in a test trial after an acquisition trial, the animal had a normal learning ability because it well remembered the electric shock. The test trial was conducted 24 hours after the acquisition trial.

Figure 1:
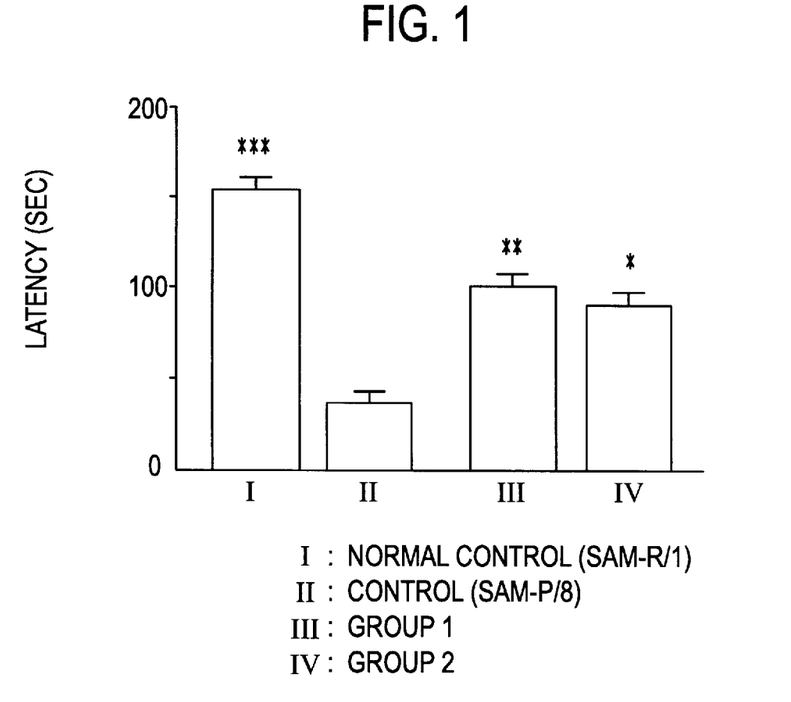
FIG. 1 shows the action of the peptide fragment of the present invention for improving learning and improving memory in the passive avoidance learning test using the strain SAM-P/8.

The peptide of the present invention was subcutaneously injected once a week since the third week after birth and its effect of improving the passive avoiding ability which was lowered in SAM-P/8 was investigated. A mouse (SAM-R/1) to which physiological saline solution was administered whereby aging proceeded normally and remembering ability did not lower was used as a normal control. An example of the results for the SAM-P/8 strain on the sixth month after birth where the 1–29 amino acid residue peptide fragment of bovine aFGF in which Cys, an amino acid at the 16-position, was substituted with Ala (150 µg/kg/day; group 1) and where the 1–15 amino acid residue fragment of bovine aFGF (80 µg/kg/day; group 2) were administered is given in FIG. 1 (t-test; *: p<0.05; : p<0.01; *: p<0.001). The results obtained for the control (SAM-P/8) and the normal control (SAM-R/1), neither of which were administered the compounds of the present invention, are also shown in FIG. 1. As shown in FIG. 1 the latency (seconds) was unexpectedly higher for the Group 1 and Group 2 mice compared to the latency of the control (SAM-P/8) mice.

(2) Water maze task (Morris' water maze task).

Figure 2:
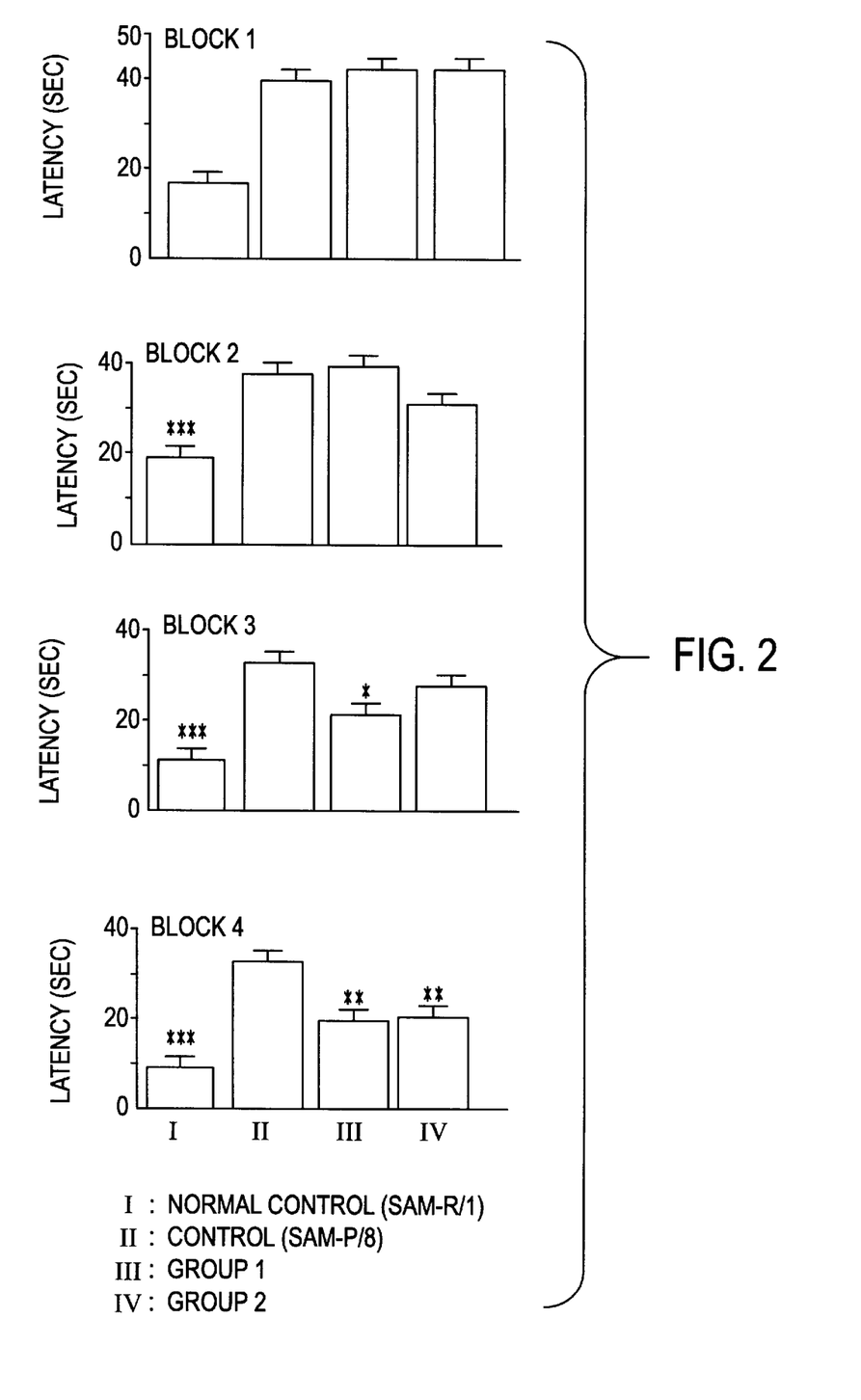
FIG. 2 shows the action of the peptide fragment of the present invention for improving the space-recognizing ability reduced in the strain SAM-P/8 in the maze-learning test in water. The index is the diving time of a mouse until it escaped to the platform.
Figure 3:
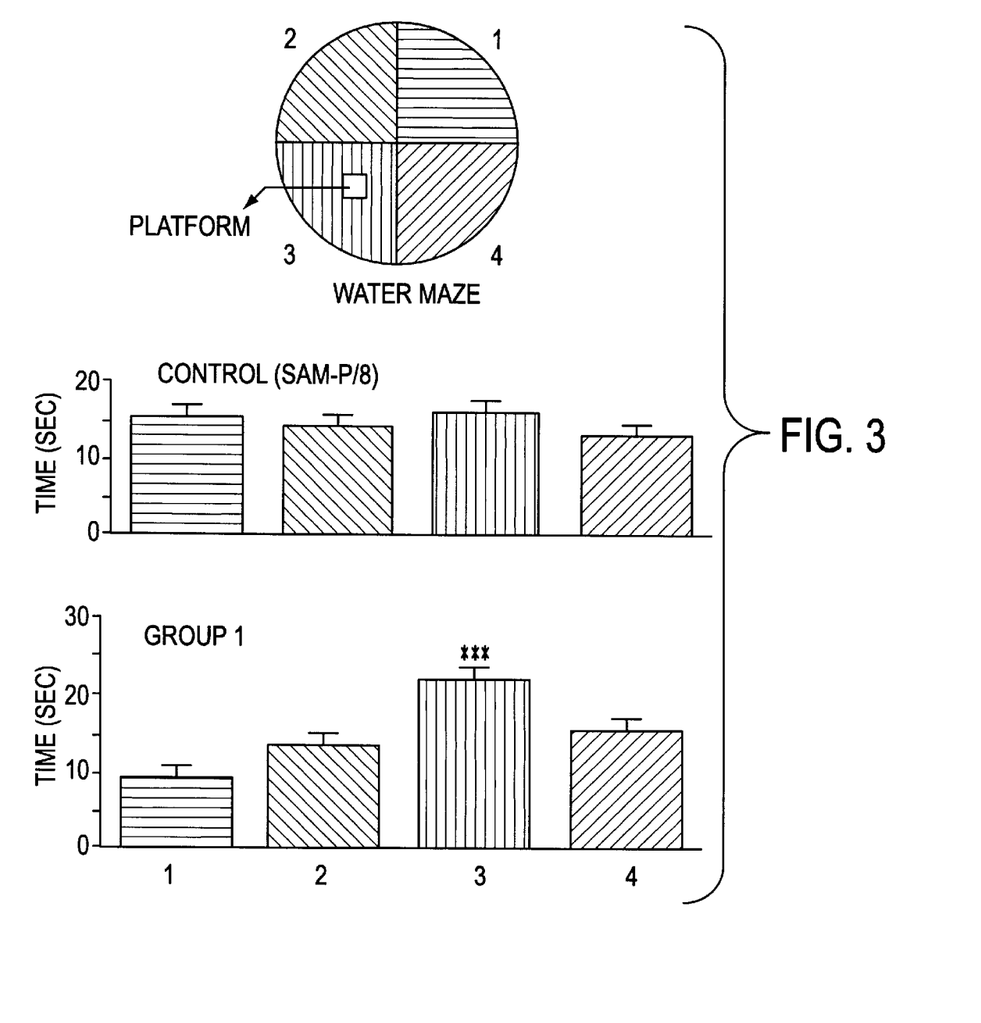
FIG. 3 shows the action of the peptide fragment of the present invention for improving the cerebral function in the maze-learning test in water in the same manner as in FIG. 2. This is a result obtained where the staying time of the mouse in each of the divided four areas is used as an index.

A platform was placed at 1 cm under the water surface in a circular swimming pool for the experiment and then fine Styrofoam beads were uniformly sprinkled onto the water surface so that a mouse was unable to recognize the platform. Any hint to the mouse in the space around the device (such as persons in charge of the experiment, table, fluorescent light and machines for the experiment) was always kept constant during the experimental period. On the day of the experiment, the pool was divided into four equal areas as shown in FIG. 3. Four starting points were randomly selected, a mouse was placed into the water, turning its head to the wall of the pool, and its diving time until it escaped to the platform was measured. When the mouse climbed up to the platform, it was left as it was for 15 seconds. When the mouse did not climb up even after 120 seconds, the trial was terminated at that time and the mouse was placed on the platform, left as it was for 15 seconds the same as above, and the diving time was recorded as 120 seconds. The case from one starting point was defined as one trial and four trials were done every ten minutes and defined as one block. Four blocks were carried out in total every other day. Senility-accelerated mice (SAM-P/8) which were not administered any compounds of the present invention were used as a control. A mouse (SAM-R/1) to which physiological saline solution was administered whereby aging proceeded and remembering ability did not decrease was used as a normal control. The peptide of the present invention was administered to the senility-accelerated mouse of the SAM-P/8 strain in the same manner as described above for the passive avoiding learning test. An example of the results of the test of learning acceleration effect in the ninth month from birth is given in FIG. 2. As shown in FIG. 2, the diving time (latency) unexpectedly decreased from Block 1 to Block 4 for the Group 1 and Group 2 mice compared to the decrease for the control (SAM-P/8) mice.

After the above-mentioned four blocks were conducted, the platform was removed, the mouse was permitted to swim for a certain period, and the time for swimming in each of the four areas was measured. When the mouse recognized and remembered the location of the platform, it stayed for a long time at the place where the platform was. Therefore, the learning and remembering abilities could be determined measuring the staying time in each of the four areas. An example of the results is given in FIG. 3. As shown in FIG. 3 the staying time in area 3, where the platform was located, was unexpectedly higher for the Group 1 mice than for the control (SAM-P/8) mice (t-test; ***: p<0.001).

(3) Protective effect on cerebral neurons.

Additionally, the effects of the peptides of the present invention on neuronal death in the CA1 subfields of the hippocampus were tested as follows:

The peptide fragment of the present invention, the 1–29 amino acid residue peptide fragment of bovine aFGF in which Cys, an amino acid at the 16-position, was substituted with Ala or the 1–29 amino acid residue peptide fragment of bovine aFGF in which Cys, an amino acid at the 16-position, was substituted with Ser, was administered by continuous intracerebroventricular infusion (850 µg/ml. respectively) into the lateral cerebral ventricles of Wister-strain rat (250–300 g. 4 rats/a group) and their common carotid arteries were occluded for 15 minutes to induce ischemic insult. Five days after ischemia, the rats were deeply anesthetized with sodium pentobarbital and transcardially perfused. Then, the brains were frozen and cut coronally in 20 µm sections by microtomy, and stained by Nissl bodies. The sections were examined by histological analysis. As a result of the analyses, the protecting effect of the peptide of the present invention on neuronal death in the CA1 subfields of the hippocampus was observed (Ala-substituted peptide; 3/4 rats, Ser-substituted peptide; 4/4 rats).

As shown in FIG. 1, when the peptide fragment of the present invention is administered to senility-accelerated mice of an SAM-P/8 strain exhibiting disabled learning and remembering with aging in the passive avoidance learning test, an action of significantly improving the reduced acquiring and maintaining abilities for remembering and learning in the SAM-P/8 strain was noted. The space-recognizing ability of the SAM-P/8 strain was reduced in the maze-learning test in water too (of FIGS. 2 and 3) but the peptide fragment of the present invention showed an action of a significant improvement for space-recognizing ability. In addition, a 1–15 amino acid residue fragment of an aFGF having a shorter chain length than the 1–29 amino acid peptide fragment of the present invention also showed an excellent action of improving the disabled learning and remembering behavior. It was also observed that the peptide fragments of the present invention exhibit protective effects against the death of cerebral neurons caused by ischemia.

It is apparent from the above-mentioned results of pharmacological tests that the peptide fragments of the present invention exhibit excellent actions of improving the cerebral functions and protecting the cerebral neurons. Consequently, the peptide fragments of the present invention are highly useful in the therapeutic treatment of diseases and conditions resulting in reduced cerebral functions such as: (1) diseases caused by degeneration of the brain (e.g. Alzheimer disease, senile dementia, Pick disease, Hungtington chorea, Parkinson disease, Parkinsonism dementia syndrome, progressive subcortical glyosis, progressive supranuclear paralysis, thalamic degeneration, hereditary aphasia and myoclonus epilepsy), (2) cerebrovascular disturbance (e.g. cerebral arteriosclerosis), (3) infectious and inflammatory diseases of the brain (e.g. progressive paralysis, various encephalitises, Creutzfeld-Jakob disease, subacute sclerosing panencephalitis, progressive multifocal leucoencephalopathy and systemic lupus erythematosus), (4) toxic brain disturbances (e.g. chronic alcoholism, carbon monoxide poisoning and heavy metal poisoning), (5) head injuries, epilepsy, brain tumor, intracranial hematoma and dialysis brain disease, and (6) ischemic cerebral diseases (e.g. cerebral infarction and cerebral thrombosis). In addition, the peptides of the present invention are useful for improvement of various symptoms which accompany diseases resulting in reduced cerebral function such as hypomnesia, aphasia, disturbance of consciousness, depressive state, indifference, delusion and confusion.

The compounds of the present invention, which include the peptide fragments of the present invention and their pharmaceutically acceptable salts, can be made into a pharmaceutical agent by combining one or more of the compounds with at least one suitable pharmaceutically acceptable carrier or diluent. The peptide fragments and their salts can be made into pharmaceutical preparations by any conventional method.

The compounds of the present invention may be used either solely or jointly in pharmaceutically effective amounts for treating animals or humans. In the prescription, the peptide fragments of the present invention may be used in the form of their pharmaceutically acceptable salts. The peptide fragments and their salts may be used either solely or jointly in pharmaceutically acceptable amounts together with pharmaceutically acceptable amounts of other pharmaceutically active ingredients in pharmaceutical compositions or preparations.

Since the compound of the present invention is a peptide, it is conventional that it is usually prepared as an injection solution. Thus, one or more of the compounds of the present invention may be prepared in the form of a solution or suspension in pharmaceutically acceptable carriers such as an aqueous or nonaqueous solvent. Examples of solvents which may be used are distilled water for injection, physiological saline solution, Ringer's solution, plant oil, synthetic fatty acid glycerides, esters of higher fatty acids, and propylene glycol. In addition, frequently-used additives for pharmaceuticals such as stabilizers, buffers, suspending agents, isotonic agents, pH-adjusting agents, antiseptics and preservatives may also be included in the preparations in conventional amounts. It is also possible, depending upon the type of the disease, to prepare other pharmaceutical compositions containing one or more of the compounds of the present invention, which are optimum for the therapy of the disease. For example, special preparations whereby the compound is not decomposed even by oral administration, may be prepared for oral administration.

What is claimed is:

1. A 1–29 amino acid residue peptide fragment of human acid fibroblast growth factor in which cysteine at the 16-position is substituted with another amino acid, or a pharmaceutically acceptable salt of the peptide fragment.

2. A peptide fragment as claimed in claim 1 wherein the 16-position is substituted with an α-amino acid.

3. A peptide fragment as claimed in claim 2 wherein said α-amino acid is selected from the group consisting of alanine, serine, and glutamic acid.

4. A pharmaceutical composition comprising a pharmaceutically effective amount of the peptide fragment or salt as claimed in claim 1, and a pharmaceutically acceptable carrier.

5. A peptide fragment having the formula (I):

$$\begin{array}{l}\text{H—Phe—Asn—Leu—Pro—Pro—Gly—Asn—Tyr—Lys—Lys—Pro—Lys—Leu—Leu—Tyr—X—} \\ \text{Ser—Asn—Gly—Gly—His—Phe—Leu—Arg—Ile—Leu—Pro—Asp—Gly—Y}\end{array} \quad (I)$$

wherein X is Ala (SEQ ID NO: 2 or SEQ ID NO: 6), Ser (SEQ ID NO: 3 or SEQ ID NO: 7) or Glu (SEQ ID NO: 4 or SEQ ID NO: 8) and Y is OH or $NH_2$, or a pharmaceutically acceptable salt of the peptide fragment of formula (I).

6. A method for treating diseases or conditions resulting in reduced cerebral functions comprising administering to a patient in need of such treatment a therapeutic amount of a peptide fragment or salt as claimed in claim 5.

7. A method for preventing the death of cerebral neurons caused by ischemia comprising administering to a patient in need of such treatment a therapeutic amount of a peptide fragment or salt as claimed in claim 5.

8. A method for treating diseases or conditions resulting in reduced cerebral functions comprising administering to a patient in need of such treatment a therapeutic amount of a peptide fragment having the formula (III):

wherein Y is OH (SEQ ID NO: 9) or $NH_2$ (SEQ ID NO: 10), or a pharmaceutically acceptable salt of the peptide fragment of formula (III).

9. A method for treating diseases or conditions resulting in reduced cerebral functions, comprising administering to a patient in need of such treatment a therapeutic amount of a peptide fragment having the formula (IV):

$$\text{H—Phe—Asn—Leu—Pro—Pro—Gly—Asn—Tyr—Lys—Lys—Pro—Lys—Leu—Leu—Tyr—Y} \quad (III)$$

wherein Y is OH (SEQ ID NO: 19) or NH$_2$ (SEQ ID NO: 20), or a pharmaceutically acceptable salt of the peptide fragment of formula (IV).

10. A method as claimed in claim 9 wherein Y is OH (SEQ ID NO: 19).

11. A method for preventing the death of cerebral neurons caused by ischemia, comprising administering to a patient in need of such treatment a therapeutic amount of a peptide fragment having the formula (III):

wherein Y is OH (SEQ ID NO: 9) or NH$_2$ (SEQ ID NO: 10), or a pharmaceutically acceptable salt of the peptide fragment of formula (III).

12. A method for preventing the death of cerebral neurons caused by ischemia, comprising administering to a patient in need of such treatment a therapeutic amount of a peptide fragment having the formula (IV):

wherein Y is OH (SEQ ID NO: 19) or NH$_2$ (SEQ ID NO: 20), or a pharmaceutically acceptable salt of the peptide fragment of formula (IV).

13. A method as claimed in claim 12 wherein Y is OH (SEQ ID NO: 19).

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( v i ) ORIGINAL SOURCE:
        ( A ) ORGANISM: Homo sapiens     ( i x ) FEATURE:
        ( A ) NAME/KEY: Modified-site
        ( B ) LOCATION: 16
        ( D ) OTHER INFORMATION: /product= "Xaa is any amino acid
            other than Cysteine."

( x i ) SEQUENCE DESCRIPTION: SEQ ID NO:1:

```
Phe  Asn  Leu  Pro  Pro  Gly  Asn  Tyr  Lys  Lys  Pro  Lys  Leu  Leu  Tyr  Xaa
1                   5                        10                            15

Ser  Asn  Gly  Gly  His  Phe  Leu  Arg  Ile  Leu  Pro  Asp  Gly
                    20                  25
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear     ( i i ) MOLECULE TYPE: peptide     ( i i i ) HYPOTHETICAL: NO     ( i v ) ANTI-SENSE: NO ( v ) FRAGMENT TYPE: N-terminal ( v i ) ORIGINAL SOURCE:
    ( A ) ORGANISM: Homo sapiens ( x i ) SEQUENCE DESCRIPTION: SEQ ID NO:2:

```
Phe Asn Leu Pro Pro Gly Asn Tyr Lys Lys Pro Lys Leu Leu Tyr Ala
1               5                   10                  15
Ser Asn Gly Gly His Phe Leu Arg Ile Leu Pro Asp Gly
            20                  25
```

( 2 ) INFORMATION FOR SEQ ID NO:3:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( v i ) ORIGINAL SOURCE:
        ( A ) ORGANISM: Homo sapiens     ( x i ) SEQUENCE DESCRIPTION: SEQ ID NO:3:

```
Phe Asn Leu Pro Pro Gly Asn Tyr Lys Lys Pro Lys Leu Leu Tyr Ser
1               5                   10                  15
Ser Asn Gly Gly His Phe Leu Arg Ile Leu Pro Asp Gly
            20                  25
```

( 2 ) INFORMATION FOR SEQ ID NO:4:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( v i ) ORIGINAL SOURCE:
        ( A ) ORGANISM: Homo sapiens     ( x i ) SEQUENCE DESCRIPTION: SEQ ID NO:4:

```
Phe Asn Leu Pro Pro Gly Asn Tyr Lys Lys Pro Lys Leu Leu Tyr Glu
1               5                   10                  15
Ser Asn Gly Gly His Phe Leu Arg Ile Leu Pro Asp Gly
            20                  25
```

( 2 ) INFORMATION FOR SEQ ID NO:5:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear     ( i i ) MOLECULE TYPE: peptide (  i  i  i ) HYPOTHETICAL: NO (  i  v ) ANTI-SENSE: NO ( v ) FRAGMENT TYPE: N-terminal ( v i ) ORIGINAL SOURCE:
    ( A ) ORGANISM: Homo sapiens ( i x ) FEATURE:
    ( A ) NAME/KEY: Modified-site
    ( B ) LOCATION: 16
    ( D ) OTHER INFORMATION: /product= "Xaa is any amino acid
        other than Cysteine."

( i x ) FEATURE:
    ( A ) NAME/KEY: Modified-site
    ( B ) LOCATION: 29
    ( D ) OTHER INFORMATION: /product= "Xaa is the amide form of
        Glycine."

( x i ) SEQUENCE DESCRIPTION: SEQ ID NO:5:

```
Phe Asn Leu Pro Pro Gly Asn Tyr Lys Lys Pro Lys Leu Leu Tyr Xaa
1               5                   10                  15
Ser Asn Gly Gly His Phe Leu Arg Ile Leu Pro Asp Xaa
            20                  25
```

( 2 ) INFORMATION FOR SEQ ID NO:6:

( i ) SEQUENCE CHARACTERISTICS:
    ( A ) LENGTH: 29 amino acids
    ( B ) TYPE: amino acid
    ( C ) STRANDEDNESS:
    ( D ) TOPOLOGY: linear ( i i ) MOLECULE TYPE: peptide (  i  i  i ) HYPOTHETICAL: NO (  i  v ) ANTI-SENSE: NO ( v ) FRAGMENT TYPE: N-terminal ( v i ) ORIGINAL SOURCE:
    ( A ) ORGANISM: Homo sapiens ( i x ) FEATURE:
    ( A ) NAME/KEY: Modified-site
    ( B ) LOCATION: 29
    ( D ) OTHER INFORMATION: /product= "Xaa is the amide form of
        Glycine."

( x i ) SEQUENCE DESCRIPTION: SEQ ID NO:6:

```
Phe Asn Leu Pro Pro Gly Asn Tyr Lys Lys Pro Lys Leu Leu Tyr Ala
1               5                   10                  15
Ser Asn Gly Gly His Phe Leu Arg Ile Leu Pro Asp Xaa
            20                  25
```

( 2 ) INFORMATION FOR SEQ ID NO:7:

( i ) SEQUENCE CHARACTERISTICS:
    ( A ) LENGTH: 29 amino acids
    ( B ) TYPE: amino acid
    ( C ) STRANDEDNESS:
    ( D ) TOPOLOGY: linear ( i i ) MOLECULE TYPE: peptide (  i  i  i ) HYPOTHETICAL: NO (  i  v ) ANTI-SENSE: NO ( v ) FRAGMENT TYPE: N-terminal ( v i ) ORIGINAL SOURCE:
    ( A ) ORGANISM: Homo sapiens ( i x ) FEATURE:
    ( A ) NAME/KEY: Modified-site
    ( B ) LOCATION: 29
    ( D ) OTHER INFORMATION: /product= "Xaa is the amide form of Glycine."

( x i ) SEQUENCE DESCRIPTION: SEQ ID NO:7:

Phe Asn Leu Pro Pro Gly Asn Tyr Lys Lys Pro Lys Leu Leu Tyr Ser
1               5                   10                  15
Ser Asn Gly Gly His Phe Leu Arg Ile Leu Pro Asp Xaa
            20                  25

( 2 ) INFORMATION FOR SEQ ID NO:8:

( i ) SEQUENCE CHARACTERISTICS:
    ( A ) LENGTH: 29 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Homo sapiens ( i x ) FEATURE:
    ( A ) NAME/KEY: Modified-site
    ( B ) LOCATION: 29
    ( D ) OTHER INFORMATION: /product= "Xaa is the amide form of Glycine."

( x i ) SEQUENCE DESCRIPTION: SEQ ID NO:8:

Phe Asn Leu Pro Pro Gly Asn Tyr Lys Lys Pro Lys Leu Leu Tyr Glu
1               5                   10                  15
Ser Asn Gly Gly His Phe Leu Arg Ile Leu Pro Asp Xaa
            20                  25

( 2 ) INFORMATION FOR SEQ ID NO:9:

( i ) SEQUENCE CHARACTERISTICS:
    ( A ) LENGTH: 15 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Homo sapiens ( x i ) SEQUENCE DESCRIPTION: SEQ ID NO:9:

Phe Asn Leu Pro Pro Gly Asn Tyr Lys Lys Pro Lys Leu Leu Tyr
1               5                   10                  15

( 2 ) INFORMATION FOR SEQ ID NO:10:

( i ) SEQUENCE CHARACTERISTICS:

(A) LENGTH: 15 amino acids
                (B) TYPE: amino acid
                (C) STRANDEDNESS:
                (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
                (A) ORGANISM: Homo sapiens (ix) FEATURE:
                (A) NAME/KEY: Modified-site
                (B) LOCATION: 15
                (D) OTHER INFORMATION: /product= "Xaa is the amide form of
                    Tyrosine."

(xi) SEQUENCE DESCRIPTION: SEQ ID NO:10:

Phe  Asn  Leu  Pro  Pro  Gly  Asn  Tyr  Lys  Lys  Pro  Lys  Leu  Leu  Xaa
1              5                        10                       15

(2) INFORMATION FOR SEQ ID NO:11:

(i) SEQUENCE CHARACTERISTICS:
                (A) LENGTH: 29 amino acids
                (B) TYPE: amino acid
                (C) STRANDEDNESS:
                (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
                (A) ORGANISM: Bos taurus (ix) FEATURE:
                (A) NAME/KEY: Modified-site
                (B) LOCATION: 16
                (D) OTHER INFORMATION: /product= "Xaa is any amino acid
                    other than Cysteine."

(xi) SEQUENCE DESCRIPTION: SEQ ID NO:11:

Phe  Asn  Leu  Pro  Leu  Gly  Asn  Tyr  Lys  Lys  Pro  Lys  Leu  Leu  Tyr  Xaa
1              5                        10                       15

Ser  Asn  Gly  Gly  Thr  Phe  Leu  Arg  Ile  Leu  Pro  Asp  Gly
              20                   25

(2) INFORMATION FOR SEQ ID NO:12:

(i) SEQUENCE CHARACTERISTICS:
                (A) LENGTH: 29 amino acids
                (B) TYPE: amino acid
                (C) STRANDEDNESS:
                (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
                (A) ORGANISM: Bos taurus ( x i ) SEQUENCE DESCRIPTION: SEQ ID NO:12:

Phe Asn Leu Pro Leu Gly Asn Tyr Lys Lys Pro Lys Leu Leu Tyr Ala
1               5                   10                  15

Ser Asn Gly Gly Thr Phe Leu Arg Ile Leu Pro Asp Gly
                20                  25

( 2 ) INFORMATION FOR SEQ ID NO:13:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( v i ) ORIGINAL SOURCE:
        ( A ) ORGANISM: Bos taurus     ( x i ) SEQUENCE DESCRIPTION: SEQ ID NO:13:

Phe Asn Leu Pro Leu Gly Asn Tyr Lys Lys Pro Lys Leu Leu Tyr Ser
1               5                   10                  15

Ser Asn Gly Gly Thr Phe Leu Arg Ile Leu Pro Asp Gly
                20                  25

( 2 ) INFORMATION FOR SEQ ID NO:14:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( v i ) ORIGINAL SOURCE:
        ( A ) ORGANISM: Bos taurus     ( x i ) SEQUENCE DESCRIPTION: SEQ ID NO:14:

Phe Asn Leu Pro Leu Gly Asn Tyr Lys Lys Pro Lys Leu Leu Tyr Glu
1               5                   10                  15

Ser Asn Gly Gly Thr Phe Leu Arg Ile Leu Pro Asp Gly
                20                  25

( 2 ) INFORMATION FOR SEQ ID NO:15:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear     ( i i ) MOLECULE TYPE: peptide     ( i i i ) HYPOTHETICAL: NO     ( i v ) ANTI-SENSE: NO ( v ) FRAGMENT TYPE: N-terminal ( v i ) ORIGINAL SOURCE:
    ( A ) ORGANISM: Bos taurus ( i x ) FEATURE:
    ( A ) NAME/KEY: Modified-site
    ( B ) LOCATION: 16
    ( D ) OTHER INFORMATION: /product= "Xaa is any amino acid other than Cysteine."

( i x ) FEATURE:
    ( A ) NAME/KEY: Modified-site
    ( B ) LOCATION: 29
    ( D ) OTHER INFORMATION: /product= "Xaa is the amide form of Glycine."

( x i ) SEQUENCE DESCRIPTION: SEQ ID NO:15:

Phe Asn Leu Pro Leu Gly Asn Tyr Lys Lys Pro Lys Leu Leu Tyr Xaa
1               5                   10                  15
Ser Asn Gly Gly Thr Phe Leu Arg Ile Leu Pro Asp Xaa
            20                  25

( 2 ) INFORMATION FOR SEQ ID NO:16:

( i ) SEQUENCE CHARACTERISTICS:
    ( A ) LENGTH: 29 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Bos taurus ( i x ) FEATURE:
    ( A ) NAME/KEY: Modified-site
    ( B ) LOCATION: 29
    ( D ) OTHER INFORMATION: /product= "Xaa is the amide form of Glycine."

( x i ) SEQUENCE DESCRIPTION: SEQ ID NO:16:

Phe Asn Leu Pro Leu Gly Asn Tyr Lys Lys Pro Lys Leu Leu Tyr Ala
1               5                   10                  15
Ser Asn Gly Gly Thr Phe Leu Arg Ile Leu Pro Asp Xaa
            20                  25

( 2 ) INFORMATION FOR SEQ ID NO:17:

( i ) SEQUENCE CHARACTERISTICS:
    ( A ) LENGTH: 29 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Bos taurus ( i x ) FEATURE:

(A) NAME/KEY: Modified-site
(B) LOCATION: 29
(D) OTHER INFORMATION: /product= "Xaa is the amide form of Glycine."

(xi) SEQUENCE DESCRIPTION: SEQ ID NO:17:

```
Phe Asn Leu Pro Leu Gly Asn Tyr Lys Lys Pro Lys Leu Leu Tyr Ser
1               5                   10                  15
Ser Asn Gly Gly Thr Phe Leu Arg Ile Leu Pro Asp Xaa
                20                  25
```

(2) INFORMATION FOR SEQ ID NO:18:

(i) SEQUENCE CHARACTERISTICS:
        (A) LENGTH: 29 amino acids
        (B) TYPE: amino acid
        (C) STRANDEDNESS:
        (D) TOPOLOGY: linear     (ii) MOLECULE TYPE: peptide     (iii) HYPOTHETICAL: NO     (iv) ANTI-SENSE: NO     (v) FRAGMENT TYPE: N-terminal     (vi) ORIGINAL SOURCE:
        (A) ORGANISM: Bos taurus     (ix) FEATURE:
        (A) NAME/KEY: Modified-site
        (B) LOCATION: 29
        (D) OTHER INFORMATION: /product= "Xaa is the amide form of Glycine."

(xi) SEQUENCE DESCRIPTION: SEQ ID NO:18:

```
Phe Asn Leu Pro Leu Gly Asn Tyr Lys Lys Pro Lys Leu Leu Tyr Glu
1               5                   10                  15
Ser Asn Gly Gly Thr Phe Leu Arg Ile Leu Pro Asp Xaa
                20                  25
```

(2) INFORMATION FOR SEQ ID NO:19:

(i) SEQUENCE CHARACTERISTICS:
        (A) LENGTH: 15 amino acids
        (B) TYPE: amino acid
        (C) STRANDEDNESS:
        (D) TOPOLOGY: linear     (ii) MOLECULE TYPE: peptide     (iii) HYPOTHETICAL: NO     (iv) ANTI-SENSE: NO     (v) FRAGMENT TYPE: N-terminal     (vi) ORIGINAL SOURCE:
        (A) ORGANISM: Bos taurus     (xi) SEQUENCE DESCRIPTION: SEQ ID NO:19:

```
Phe Asn Leu Pro Leu Gly Asn Tyr Lys Lys Pro Lys Leu Leu Tyr
1               5                   10                  15
```

(2) INFORMATION FOR SEQ ID NO:20:

(i) SEQUENCE CHARACTERISTICS:
        (A) LENGTH: 15 amino acids
        (B) TYPE: amino acid
        (C) STRANDEDNESS:
        (D) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
                ( A ) ORGANISM: Bos taurus ( i x ) FEATURE:
                ( A ) NAME/KEY: Modified-site
                ( B ) LOCATION: 15
                ( D ) OTHER INFORMATION: /product= "Xaa is the amide form of
                        Tyrosine."

( x i ) SEQUENCE DESCRIPTION: SEQ ID NO:20:

Phe Asn Leu Pro Leu Gly Asn Tyr Lys Lys Pro Lys Leu Leu Xaa
1               5                   1 0                  1 5